United States Patent [19]

Futami et al.

[11] Patent Number: 4,970,245

[45] Date of Patent: Nov. 13, 1990

[54] DENTAL HEAT-CURING SILICONE COMPOSITIONS

[75] Inventors: Shunichi Futami, Nagareyama; Nobuko Okita, Tokyo, both of Japan

[73] Assignee: G-C Dental Industrial Corp., Tokyo, Japan

[21] Appl. No.: 304,559

[22] Filed: Feb. 1, 1989

[30] Foreign Application Priority Data

Feb. 5, 1988 [JP] Japan .................................. 63-23834

[51] Int. Cl.$^5$ ................................................ A61K 6/10
[52] U.S. Cl. ...................................... 523/109; 525/100
[58] Field of Search .......................... 523/109; 525/100

[56] References Cited

U.S. PATENT DOCUMENTS 4,293,677 10/1981 Imai ..................................... 525/100
4,766,176 8/1988 Lee et al. ............................. 525/100

FOREIGN PATENT DOCUMENTS 1089009 11/1967 United Kingdom .
2193722 2/1988 United Kingdom .

*Primary Examiner*—Melvyn L. Marquis
*Attorney, Agent, or Firm*—Oblon, Spivak, McClelland, Maier & Neustadt

[57] ABSTRACT

A dental heat-curing silicone composition comprising components A and B obtained by adding inorganic fillers, and if required coloring agents an conventional additives to ingredient of an organopolysiloxane having at least two vinyl groups per molecule, and ingredient of an organohydropolysiloxane having two hydrogen atoms bonded at least to silicone per molecule, and further including 10 parts by weight to 50 parts by weight inclusive of a powder of (neth)acrylate ester homopolymer and/or a (meth)acrylate ester copolymer per a toatl of 100 parts by weight of the components A and B.

8 Claims, No Drawings

DENTAL HEAT-CURING SILICONE COMPOSITIONS

BACKGROUND OF THE INVENTION

1. Field of the Invention

The present invention relates generally to a material for lining the mucosal surfaces of denture plates with a silicone rubber base soft material and, more particularly, to a dental heat-curing silicone composition for lining denture plates, which is well bondable to dentures without recourse to any bonding agent.

2. Statement of the Prior Art

In most cases, patients for whom dentures, esp., full dentures are required are so far advanced in years that their alveolar ridges generally suffer from striking deossification and bear an increased occulsal force per unit area. Since the mucosae of their alveolar ridges are also thinned due to geriatric atrophy, occlusal and mastication impacts are not mitigated, and are thus transmitted directly to the alveolar bones. Further, the thinned mucosae sandwiched between hard resin denture plates and the hard alveolar bones are squeezed whenever occlusion occurs, so that they are injured with pains.

In such serious cases, any satisfactory results cannot be obtained with the maintenance, stability and support of dentures by preparing denture plates only with methyl methacrylate resins heretofore used. It is then required to line the mucosal surfaces of resin denture plates with a soft material, a so-called "soft liner" to make up for the lost viscoelasticity of alveolar ridge mucosae and produce a cushion effect to mitigate occlusal impacts. In short, it is the object of soft material-lining to overcome various troubles caused by the pressure of hard materials of denture plates upon the mucosae under the plates.

Until now, (meth)acrylates ester polymers, polyvinyl chloride copolymers, silicone resins, etc. have been clinically used as such soft liners. Further proposal has been made of fluorine base liners, polyolefinic base liners and silicone rubber base liners. For temporal uses, denture stabilizers have been applied.

However, liners such as (meth)acrylate polymers, polyvinyl chloride copolymers and silicone resins etc. were so poor in chemical stability in the oral cavities that they could not be used over an extended period of time, since they were hardened, embrittled, discolored and released from resin denture plates within several months. The fluorine base liners are also too poor in viscoelasticity to produce a sufficient cushion effect. The polyolefinic base liners are of no practical use, since their elevated polymerization temperature tends to deform resin denture plates and they require a plurality of bonding agents and an exclusive heater which make manipulations complicated. Although the silicone rubber base liners are very stable materials, yet no sufficient adhesion to resin denture plates are obtained for that reason and also manipulations are troublesome.

The denture stabilizers, when used over an extended period of time, increase in visco-consistency and decrease in plasticity. As a result, they did not only fully achieve the object of enhancing the maintenance, stabilization and support of denture plates by improvements in the fitness and periphery sealability of unfit dentures, but often cause troubles in oral structures. Due to their low compression stress and poor elasticity, they could not produce any sufficient cushion effect upon occulsal pressures, and were responsible for the recurrence of pains in oral mucosae.

As mentioned above, the soft liners for denture plates heretofore provided were by no means suitable for practical use, since they could be used only for a short period of time in the oral cavities and failed to produce any satisfactory cushion effect and, to add to this, their use was so complicated that they hardly bear practical use. For that reason, there has been a demand for a soft liner excelling in the adhesion to resin denture plates and possessing a suitable viscoelasticity but undergoing neither a lowering of physical properties nor deposition of microorganisms, etc. With the society of aging population in particular, there has been a strong demand for such a soft liner.

SUMMARY OF THE INVENTION

In order to solve such problems as mentioned in connection with the prior art, the present inventors have made intensive and extensive studies of a material excelling in the permanent adhesion to resin denture plates and durability, possessing a suitable viscoelasticity and being easily applicable only with recourse to conventionally available dental techniques. As a result, it has been found that a clinically satisfactory silicone rubber base liner is obtainable by adding to a heat-curing vinyl silicone composition of the addition polymerization type 10 parts by weight to 50 parts by weight inclusive of a (meth)acrylate ester homopolymer and/or a (meth)acrylate ester copolymer. More surprisingly, it has been discovered that the (meth)acrylate ester homopolymer and/or (meth)acrylate ester copolymer, that is a starting material for resin denture plates, can be much more improved in terms of the adhesion to resin denture plates by the addition thereto of a heat-curing vinyl silicone composition of the addition polymerization type. As the (meth)acrylate ester homopolymers and/or (meth)acrylate ester copolymers usable in the present invention, use may practically and preferably be made of those generally used for denture plates such as, for instance, homopolymers such as methyl methacrylate, ethyl methacrylate, propyl methacrylate, allyl methacrylate and butyl methacrylate and copolymers such as methyl methacrylate/ethyl methacrylate, methyl methacrylate/butyl methacrylate and methyl methacrylate/allyl methacrylate. The (meth)acrylate ester homopolymers and (meth)acrylate ester copolymers may be used alone or in combination. In an amount of less than 10 parts by weight per 100 parts by weight of the heat-curing vinyl silicone composition of the addition polymerization type, the (meth)acrylate ester homopolymers and/or (meth)acrylate ester copolymers are found to give rise to neither substantial improvements in nor satisfactory effect upon adhesive force. In an amount exceeding 50 parts by weight, the resulting composition decreases considerably in rubber elasticity and hardens, so that there is a marked decrease in the cushion effect upon dentures. In consequence, it loses the properties of being able to be used as soft liners and, hence, becomes unsuitable. Therefore, the proportion of the (meth)acrylate ester homopolymers and/or (meth)acrylate ester copolymers added to and incorporated into the heat-curing vinyl silicone compositions of the addition polymerization type is limited to 10 parts by weight to 50 parts by weight inclusive. Although the (meth)acrylate esters may appear in the form of liquid monomers to rubbery polymers, their homopolymers and copolymers reducible to fine powders have an average molecular weight of 50,000 or more. A polymer having a molecular weight exceeding 2,000,000 is unpreferred, because its wetting-out with respect to resin monomers is so insufficient that there is rather a decrease in bond strength. Therefore, the average molecular weight of the (meth)acrylate ester homopolymers and/or (meth)acrylate ester copolymers used in the present invention is limited to 50,000 to 2,000,000 inclusive. Coarse powder particles having a particle size exceeding 100 μm are unpreferred and unsuitable, partly because a product of a catalyst material and a base material, that is, the dental heat-curing silicone composition, is much rougher to the touch during its kneading, and partly because there is a decrease in the mechanical strength suitable for soft liners. Therefore, the particle size of the powders of the (meth)acrylate ester homopolymers and/or (meth)acrylate ester copolymers is limited to 100 μm or less. The finer the powders, the better will be the results.

In order that the dental heat-curing composition is polymerized under pressure simultaneously with the thermal polymerization of a resin in a dough stage for denture plates for bonding, it may practically comprise components (a) and (b), both in a jam-like state, into either one which the powders of the (meth)acrylate ester homopolymers and/or (meth)acrylate ester copolymers may be incorporated. In other words, the dental heat-curing vinyl silicone compositions according to the present invention comprise the heat-curing vinyl silicone compositions of the addition polymerization type to and into which the (meth)acrylate ester homopolymers and/or (meth)acrylate ester copolymers are added.

Reference will now be made in detail to the methods for the addition and incorporation of the (meth)acrylate ester homopolymers and/or (meth)acrylate ester copolymers.

1. Component A

Added to the component (a) containing an organopolysiloxane having at least two vinyl groups per molecule are inorganic fillers and the fine powders of the (meth)acrylate ester homopolymers and/or (meth)acrylate ester copolymers and, if required, conventional additives.

Component B

Added to the component (b) containing an organohydropolysiloxane having two hydrogen atoms bonded at least to silicone per molecule are inorganic fillers, the fine powders of the (meth)acrylate ester homopolymers and/or (meth)acrylate ester copolymers and, if required, conventional additives such as catalysts.

Both components A and B may be mixed together for use.

2. Added to and mixed with either one of the components (a) and (b) are inorganic fillers and the fine powders of (meth)acrylate ester homopolymers and/or (meth)acrylate ester copolymers and, if required, conventional additives such as a slight amount of catalysts for use.

As the catalysts, use in usually made of chloroplatinic acid.

The organopolysiloxanes used as the component (a) especially in dentistry are primarily polydimethylsiloxane, but may include those containing an ethyl or phenyl group as well. The organohydropolysiloxanes used as the component (b) particularly in dentistry are mainly polyhydromethylsiloxane, but may include those containing an ethyl or phenyl group as well. Of these, preference is given to the use of a silicone containing a methyl or ethyl group because of their harmlessness.

The inorganic fillers usable in the present invention may include silicic acid and its salt, metal oxides, metal hydroxides and sulfates which should have a solubility of 0.2 g or less with respect to 100 ml of water of 20° C. On the other hand, the conventional additives may include catalysts, perfumes, waxes and oily ingredients as well as ingredients for the prevention of hydrogen generation such as metallic palladium.

EXAMPLES

The present invention will now be described, specifically but not exclusively, with reference to the following examples.

EXAMPLE 1

Component A

Forty (40) parts by weight of the polydimethylsiloxane having at least two vinyl groups per molecule and 10 parts by weight of finely divided silicic anhydride were put along with 20 parts by weight of methyl methacrylate homopolymer powders (having an average molecular weight of 50,000 and an average particle size of 80 μm) and a slight amount of a pigment and a catalyst in a kneader wherein they were sufficiently kneaded together for 45 minutes into a uniform product, which was then defoamed in vacuo to obtain the component A.

Component B

Forty (40) parts by weight of the polyhydromethylsiloxane having two hydrogen atoms bonded at least to silicone per molecule were put together with 10 parts by weight of silicic anhydride in a kneader wherein they were sufficiently kneaded together for 45 minutes into a uniform product, which was then defoamed in vacuo to obtain the component B.

Mixing of Component A with Component B

In use, the components A and B are mixed together at a weight ratio of 7:5.

Adhesion to Denture

The methyl methacrylate resin was found to be firmly bonded to the denture and around its periphery. Another test piece was prepared for measurement which was found to have a bond strength of 20 kgf/cm$^2$.

EXAMPLE 2

Component A

Thirty-two (32) parts by weight of the polydimethylsiloxane having at least two vinyl groups in one molecule were put along with 18 parts by weight of light calcium carbonate and a slight amount of catalysts in a kneader wherein they were sufficiently kneaded together for 40 minutes into a uniform product, which was then defoamed in vacuo to obtain the component A.

Component B 20 parts by weight of the polyhydromethylsiloxane and 20 parts by weight of the polyhydroethylsiloxane, each having in one molecule at least two hydrogen atoms bonded to silicone were put along with 10 parts by weight of light calcium carbonate, 15 parts by weight of ethyl acrylate homopolymer powders (having an average molecular weight of 200,000 and an average particle size of 40 μm) and slight amounts of a pigment and additives in a kneader wherein they were sufficiently kneaded together for 40 minutes into a uniform product, which was in turn defoamed in vacuo to obtain the component B.

Mixing of Component A with Component B

In use, the components A and B are mixed together at a weight ratio of 10:13.

Adhesion to Denture

The methyl methacrylate resin was found to be firmly bonded to the denture and around its periphery. Another test piece was prepared for measurement which was found to have a bond strength of 21 kgf/cm$^2$.

EXAMPLE 3

Component A 22 parts by weight of the polydimethylsiloxane and 18 parts by weight of polydiethylsiloxane, each having in one molecule at least two vinyl group were put along with 10 parts by weight of talc and 12.5 parts by weight of methyl methacrylate/ethyl methacrylate copolymer powders (having an average molecular weight of 400,000 and an average particle size of 20 μm), a slight amount of catalysts and perfumes in a kneader wherein they were sufficiently kneaded together for 60 minutes into a uniform product, which was in turn defoamed in vacuo to obtain the component A.

Component B

Thirty-five (35) parts by weight of the polyhydromethylsiloxane having in one molecule at least two hydrogen atoms bonded to silicone were put along with 15 parts by weight of talc, 12.5 parts by weight of ethyl methacrylate homopolymer powders (having an average molecular weight of 400,000 and an average particle size of 20 μm) and slight amounts of a pigment and additives in a kneader wherein they were sufficiently kneaded together for 60 minutes into a uniform product, which was then defoamed in vacuo to obtain the component B.

Mixing of Component A with Component B

In use, the components A and B are mixed together at a weight ratio of 1:1.

Adhesion to Denture

The methyl methacrylate resin was found to be firmly bonded to the denture and around its periphery. Another test piece was prepared for measurement which was found to have a bond strength of 23 kgf/cm$^2$.

EXAMPLE 4

Component A

Thirty-five (35) parts by weight of the polydiethylsiloxane having at least two vinyl groups in one molecule were put along with 15 parts by weight of diatomaceous earth and 25 parts by weight of butyl methacrylate homopolymer powders (having an average molecular weight of 900,000 and an average particle size of 50 μm) and a slight amount of a catalyst in a kneader wherein they were sufficiently kneaded together for 40 minutes into a uniform product, which was then defoamed in vacuo to obtain the component A.

Component B

Thirty-three (33) parts by weight of the hydroethylsiloxane having in one molecule at least two hydrogen atoms bonded to silicone were put along with 17 parts by weight of diatomaceous earth and slight amounts of a pigment and additives in a kneader wherein they were sufficiently kneaded together for 40 minutes into a uniform product, which was then defoamed in vacuo to obtain the component B.

Mixing of Component A with Component B

In use, the components A and B are mixed together at a weight ratio of 3:2.

Adhesion to Denture

The methyl methacrylate resin was found to be firmly bonded to the denture and around its periphery. Another test piece was prepared for measurement which was found to have a bond strength of 19 kgf/cm$^2$.

EXAMPLE 5

Component A 20 parts by weight of the polydimethylsiloxane and 20 parts of the polydiethylsiloxane, each having at least two vinyl groups in one molecule were put along with 10 parts by weight of zinc oxide and slight amounts of a pigment and additives such as catalysts in a kneader wherein they were sufficiently kneaded together for 50 minutes into a uniform product, which was in turn defoamed in vacuo to obtain the component A.

Component B 20 parts by weight of the hydromethylsiloxane and 20 parts by weight of the hydroethylsiloxane, each having in one molecule at least two hydrogen atoms bonded to silicone were put along with 10 parts by weight of zinc oxide and 12.5 parts by weight of methyl methacrylate/butyl methacrylate copolymer powders (having an average molecular weight of 1,600,000 and an average particle size of 75 μm) in a kneader wherein they were sufficiently kneaded together for 50 minutes into a uniform product, which was then defoamed in vacuo to obtain the component B.

Mixing of Component A with Component B

In use, the components A and B are mixed together at a weight ratio of 4:5.

Adhesion to Denture

The methyl methacrylate resin was found to be firmly bonded to the denture and around its periphery. Another test piece was prepared for measurement which was found to have a bond strength of 20 kgf/cm$^2$.

COMPARATIVE EXAMPLE 1

Component A

Thirty-two (32) parts by weight of the polydimethylsiloxane having at least two vinyl groups in one molecule were put together with 18 parts by weight of silicic anhydride and slight amounts of pigments and additives such as catalysts in a kneader wherein they were sufficiently kneaded together for 40 minutes into a uniform product, which was then defoamed in vacuo to obtain the component A.

Component B

Thirty-five (35) parts by weight of the hydromethylsiloxane having in one molecule at least two hydrogen atoms bonded to silicone were put along with 15 parts by weight of silicic anhydride in a kneader wherein they were sufficiently kneaded together for 40 minutes into a uniform product, which was then defoamed in vacuo to obtain the component B.

Mixing of Component A with Component B

In use, the components A and B are mixed together at a weight ratio of 1:1.

Adhesion to Denture

Although the methyl methacrylate resin was firmly bonded to the alveolar ridge of the denture, yet its adhesion along the periphery was insufficient. Another test piece was prepared for measurement which was found to have a bond strength of 16 kgf/cm$^2$.

COMPARATIVE EXAMPLE 2

Component A 22 parts by weight of the polydimethylsiloxane and 18 parts by weight of the polydiethylsiloxane, each having at least two vinyl groups in one molecule were put along with 15 parts by weight of diatomaceous earth, 5 parts by weight of hexyl methacrylate homopolymer powders (having an average molecular weight of 1,000,000 and an average particle size of 150 μm) and slight amounts of a pigment and additives such as catalysts in a kneader wherein they were sufficiently kneaded together for 40 minutes into a uniform product, which was then defoamed in vacuo to obtain the component A.

Component B 35 parts by weight of the polyhydromethylsiloxane having in one molecule at least two hydrogen atoms bonded to silicone were put along with 20 parts by weight of diatomaceous earth in a kneader wherein they were sufficiently kneaded together for 40 minutes into a uniform product, which was then defoamed in vacuo to obtain the component B.

Mixing of Component A with Component B

In use, the components A and B are mixed together at a weight ratio of 1:1.

Adhesion to Denture

On the alveolar ridge and periphery of the denture, methyl methacrylate resin was found to have been partially unbonded. Another test piece was prepared for measurement which was found to have a bond strength of 11 kgf/cm$^2$.

COMPARATIVE EXAMPLE 3

A product A commercially available as silicone rubber base liners for denture plates was used according to the maker's instructions.

Adhesion to Denture

Although the methyl methacrylate resin was bonded to the alveolar ridge and periphery of the denture, yet its adhesion along the periphery was insufficient. Another test piece was prepared for measurement which was found to have a bond strength of 12 kgf/cm$^2$.

The products of Examples 1 to 5 and Comparative Examples 1 to 3 were examined in terms of the following properties. The results are set forth in a table to be given later.

Testing Methods

Manipulatability

Organoleptic estimation was made of the manipulativeness of the components A and B when they were kneaded together on a kneading sheet and when they were spread under pressure on a resin in a dough stage for denture plates with the following ranks: good: O, medium: Δ, and bad: ×.

Adhesion to Denture

According to the conventional manner for preparing dentures, a wax denture is invested in a lower portion of a dental flask with gypsum, as attached to an alveolar ridge model. After curing of gypsum, a releasing agent is applied, and a frame is attached to an upper portion of the flask, into which gypsum is then cast. The flask is thereafter lidded to pressurize the content at about 50 kgf/cm$^2$, and is allowed to stand. After curing of gypsum, the flask is immersed in water of 60° C. for about 3 minutes, and a gypsum model is then opened. The wax denture softened inside is removed, and any residues of wax are further removed in a stream of hot water to obtain a gypsum model for the polymerization of a methyl polymethacrylate denture plate. Methyl polymethacrylate powders for denture plates (which were of transparency for easy observation) and a suitable amount of liquid methyl methacrylate are kneaded together in a lidded laboratory dish, and the mixture is allowed to stand. After the mixture reachs a dough stage, it is charged in an upper portion of the gypsum model and covered with a polyethylene film. On the other hand, a dental paraffin wax sheet of 1.0 to 1.5 mm in thickness is cut to a size slightly larger than that of the lower alveolar ridge model portion of the gypsum model, and is softened and brought into pressure contact therewith. The upper portion of the gypsum model filled with the resin mixture, now like dough, is combined with this lower portion, and the assembly is pressurized at about 40 kgf/cm$^2$. The gypsum model is opened to remove the paraffin wax, and fins of the dough resin mixture and a 5 to 8 mm wide portion thereof defining the periphery of a denture are cut off. Then, the components A and B are kneaded together by a spatula on a kneading sheet for 45 seconds, and the resulting product is flatly spread thereon for defoaming. The product is thereafter sufficiently spread under pressure on the surface of the dough resin mixture from which the polyethylene film has been removed. The upper and lower portions of the gypsum model are again combined with each other, and are pressurized at about 50 kgf/cm$^2$. Afterwards, the gypsum model is transferred to a clamp, and is heated in hot water of 70° C. for 30 minutes and subsequently in boiling water for 30 minutes, as fixed to that clamp. After cooling off, a denture lined with the dental heat-curing silicone composition is removed from within the gypsum model, and is then polished by a dental abrasive material. The dentures prepared in this manner were visually observed and estimated in terms of the degree of adhesion with the following ranks, O indicating that the liners were still bonded to the dentures even upon receiving a finger push, Δ indicating that the liners were released from the dentures upon receiving a finger push, and × indicating that the liners were not bonded to the dentures from the outset.

Bond Strength

According to the method for bonding the liners to dentures, prepared is a 10 mm×10 mm×9 mm sandwiched test piece in which 3 mm thick methyl methacrylate resins for denture plates are bonded to both sides of the dental heat-curing silicone composition of 3 mm in thickness. The test piece prepared in this manner was attached to a given position of an autograph, model DSC-5000, manufactured by Shimazu Corporation, and was then subjected to vertical tensile testing at a cross head speed of 5 mm/min. to measure a resisting force at which the test piece was ruptured. The chart speed applied then was 50 mm/min.

Elastic Deformation

According to the method for bonding the liners to dentures, only the dental heat-curing silicone composition was formed to a diameter of 35 mm and a thickness of 2.0 mm. The test piece thus prepared was attached to a given position of an autograph, Model DSC-5000, manufactured by Shimazu Corporation, and it was compressed at a cross head speed of 1 mm/min. to measure a change (in %) in thickness of the test piece with respect to its original thickness at a load of 1.0 kgf/cm$^2$. Such testing conditions were determined, taking into account the fact that the thickness of a soft liner necessary and sufficient to produce a cushion effect is said to be about 2.0 mm and the maximum occlusal force of a wearer of a full denture having a plate area of 20 to 30 cm$^2$ is presumed to be about 20 kgf.

For further examination of the durability of the cured silicone compositions, dentures and sandwiched test pieces were immersed in water of 37° C. to carry out the following measurement and observation after the lapse of 6 months.

Bond Strength

Measurement was performed according to the aforesaid method.

Discoloration

The dentures and sandwiched test pieces were visually compared with the dentures just after preparation.

Deposition of Microorganisms, etc.

The deposition of microorganisms, etc. was observed under a stereoscopic microscope (×40).

The results are set out in the following table.

TABLE

| Items | | Example 1 | Example 2 | Example 3 | Example 4 |
|---|---|---|---|---|---|
| (Meth) arcylate ester homopolymer or (Meth) acrylate ester copolymer | Names | Methyl methacrylate homopolymer | Ethyl acrylate homopolymer | Ethyl methacrylate homopolymer Methyl methacrylate · Ethyl methacrylate copolymer | Buthyl methacrylate homopolymer |
| | Average molecular weight | 50,000 | 200,000 | 400,000 | 900,000 |
| | Average particle size (μm) | 80 | 40 | 20 | 50 |
| | Amount of additives (parts by weight) | 20 | 15 | 25 | 25 |
| Manipulatability | | O | O | O | O |
| Adhesion to denture | | O | O | O | O |
| Bond strength (kgf/cm$^2$) | | 20 | 21 | 23 | 19 |
| Elastic deformation (%) | | 9 | 11 | 10 | 10 |
| Durability (Immersion in 37° C. distilled water) | Bond strength (kgf/cm$^2$) | 22 | 24 | 27 | 20 |
| | Discoloration | None | None | None | None |
| | Deposition of microorganisms | None | None | None | None |
| Judgement | | O | O | O | O |

| Items | | Example 5 | Comparative Example 1 | Comparative Example 2 | Comparative Example 3 |
|---|---|---|---|---|---|
| (Meth) acrylate ester homopolymer or (Meth) acrylate ester copolymer | Names | Methyl methacrylate · Buthyl methacrylate copolymer | — | Hexyl methacrylate homopolymer | — |
| | Average molecular weight | 1,600,000 | — | 1,000,000 | — |
| | Average particle size (μm) | 75 | — | 150 | — |
| | Amount of additives (parts by weight) | 12.5 | — | 5 | — |
| Manipulatability | | O | O | Δ | Δ |
| Adhesion to denture | | O | Δ | Δ | Δ |
| Bond strength (kgf/cm$^2$) | | 20 | 16 | 11 | 12 |
| Elastic deformation (%) | | 9 | 8 | 8 | 8 |
| Durability (Immersion in 37° C. distilled water) | Bond strength (kgf/cm$^2$) | 21 | 20 | 12 | 9 |
| | Discoloration | None | None | None | Discolored |
| | Deposition of microorganisms | None | None | None | Deposited |

TABLE -continued

| Judgement | O | Δ | Δ | X |
|---|---|---|---|---|

Manipulatability

In the examples and Comparative Example 1, both components A and B had a proper viscosity, and the mixtures appeared in the form of a smooth paste having a good fluidity without sags and assuring easy manipulations. In Comparative Example 3, some sags were found. In Comparison Example 2, the hexyl methacrylate polymer powders were so coarse that the kneaded product was felt sandy to the touch.

Adhesion to Denture

In all the examples according to the present invention, firm adhesion was achieved. In Comparative Examples 1 and 3, however, the adhesion along the peripheries of dentures was weak. In Comparative Example 2, unbonded spots were scattered.

Bond Strength

Obtained in all the examples according to the present invention was a bond strength on the order of 20 kgf/cm$^2$ which showed a 25 to 44% increase with respect to the bond strength of Comparative Example 1 to which the (meth)acrylate ester homopolymer and/or (meth)acrylate ester copolymer was not added. Also, 67 to 109% improvements were achieved as compared with Comparative Examples 2 and 3.

Elastic Deformation

In the examples according to the present invention and the comparative examples, a deformation of about 10% was obtained. This indicates that a thickness of about 1.8 mm is assured even at an occlusal pressure load to produce a cushion effect.

Durability

In the examples according to the present invention and Comparative Examples 1 and 2, there achieved a 5 to 25% increase in bond strength from just after preparation. In Comparative Example 3, however, a 25% decrease was found. As regards discoloration and the deposition of microorganisms, etc. no abnormality was found in the Examples and Comparative Examples 1 and 2. In Comparative Example 3, however, striking discoloration and a number of spore-form gray to white lumps of mold were found.

According to the present invention, the dental heat-curing silicone compositions can easily be bonded to resin denture plates for lining by the same polymerization method as applied for the preparation of denture plates and conventional manipulations but without recourse to any bonding agent. The denture lined with the heat-curing silicone composition according to the present invention was applied to a patient in serious conditions caused by a sustaining pressure of the hard material of a denture plate upon the mucosa under the plate due to a remarkable deossification and incurable even by repeated rebasing of dentures. As a result, it was noted that the instability of the denture and pains at the time of mastication were eliminated. That denture could be continuously used, during which abnormal symptoms such as allergic reactions were not found. Even after the lapse of 6 months, there were not found such problems as a lowering of elasticity, discoloration, peeling-off and deposition of microorganisms, etc. It is expected that with the advent of society of aging population, there will be a steady increase in cases wherein difficulty is involved in using and wearing dentures. With the present invention taking advantage of the viscoelasticity, stability and safety of silicone rubber for soft liners, however, it is believed that such patients will be able to lead a comfortable daily life, since it is very likely that they may suffer pains at the time of occlusion and mastication.

What is claimed is:

1. A dental heat-curing silicone composition comprising a mixture of:
   (A) an organopolysiloxane having at least two vinyl groups per molecule;
   (B) an organohydropolysiloxane having at least two silicone-bonded hydrogen atoms per molecule; and
   (C) 10-50 parts by weight, inclusive, of a (meth)acrylate ester homopolymer or copolymer powder, per 100 parts by weight of components A and B.

2. The composition of claim 1, wherein said (meth)acrylate ester homopolymer or copolymer comprises monomer units of $C_{1-4}$ acrylate esters, $C_{1-4}$ methacrylate esters or mixtures thereof.

3. The composition of claim 1, wherein said (meth)acrylate ester homopolymer or copolymer has an average molecular weight of 50,000-2,000,000 inclusive.

4. The composition of claim 1, wherein said (meth)acrylate ester homopolymer or copolymer has an average particle size of 100 microns or less.

5. The composition of claim 1, wherein said composition further comprises an inorganic filler.

6. The composition of claim 1, wherein said organopolysiloxane is polydimethylsiloxane.

7. The composition of claim 1, wherein said organohydropolysiloxane is polyhydromethylsiloxane.

8. The composition of claim 5, wherein said filler is selected from the group consisting of silicic acid and salts thereof, metal oxides, metal hydroxides and metal sulfates.

* * * * *